US010092753B1

United States Patent
Howard et al.

(10) Patent No.: US 10,092,753 B1
(45) Date of Patent: Oct. 9, 2018

(54) METHOD TO ENHANCE SPECIFIC MEMORIES WITH TCS DURING SLOW-WAVE SLEEP

(71) Applicant: HRL Laboratories, LLC, Malibu, CA (US)

(72) Inventors: Michael D. Howard, Westlake Village, CA (US); Praveen K. Pilly, West Hills, CA (US); Matthias Ziegler, Oakton, VA (US); Matthew E. Phillips, Calabasas, CA (US); Rajan Bhattacharyya, Sherman Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/227,922

(22) Filed: Aug. 3, 2016

Related U.S. Application Data

(60) Provisional application No. 62/210,907, filed on Aug. 27, 2015, provisional application No. 62/210,890, filed on Aug. 27, 2015, provisional application No. 62/247,435, filed on Oct. 28, 2015.

(51) Int. Cl.
| | | |
|---|---|---|
| *A61N 1/36* | (2006.01) | |
| *A61B 5/0476* | (2006.01) | |
| *A61B 5/00* | (2006.01) | |
| *A61N 1/04* | (2006.01) | |

(52) U.S. Cl.
CPC ........ *A61N 1/36025* (2013.01); *A61B 5/0075* (2013.01); *A61B 5/0476* (2013.01); *A61B 5/4812* (2013.01); *A61B 5/4836* (2013.01); *A61B 5/7271* (2013.01); *A61N 1/0484* (2013.01)

(58) Field of Classification Search
CPC .................................................. A61N 1/36025
See application file for complete search history.

(56) References Cited

U.S. PATENT DOCUMENTS

| | | | |
|---|---|---|---|
| 8,718,778 B2 | 5/2014 | Bikson et al. | |
| 9,116,835 B1 * | 8/2015 | Smyth | A61B 5/0476 |
| 9,370,658 B2 * | 6/2016 | Neuvonen | A61N 1/36014 |
| 2009/0319002 A1 * | 12/2009 | Simon | A61N 1/0408 607/45 |
| 2012/0046531 A1 * | 2/2012 | Hua | A61B 5/6865 600/317 |
| 2012/0245653 A1 | 9/2012 | Bikson et al. | |

(Continued)

OTHER PUBLICATIONS

Tremblay, Sara, et al. "The Uncertain Outcome of Prefrontal TDCS." Brain Stimulation 7.6 (2014): 773-83. Web.*

(Continued)

*Primary Examiner* — Allen Porter, Jr.
(74) *Attorney, Agent, or Firm* — Tope-McKay & Associates

(57) ABSTRACT

Described is a system for enhancing memories during sleep. The system detects, via at least one sensor, brain activity of a user as the user learns a new episode pattern or recalls an episode pattern. The episode pattern is temporally compressed. A specific sleep stage is detected in the user. Upon detection of the specific sleep stage, the system automatically recreates the temporally compressed episode pattern by applying neural stimulation to the user to ensure the consolidation of the episode pattern in the user.

17 Claims, 6 Drawing Sheets

(56) References Cited

U.S. PATENT DOCUMENTS

| | | | | |
|---|---|---|---|---|
| 2012/0265261 | A1* | 10/2012 | Bikson | A61N 1/36025 607/2 |
| 2014/0057232 | A1* | 2/2014 | Wetmore | G09B 19/00 434/236 |
| 2015/0025590 | A1* | 1/2015 | Cheng | A61N 1/36021 607/3 |
| 2016/0175589 | A1* | 6/2016 | Wingeier | A61N 1/36025 607/45 |
| 2016/0228702 | A1* | 8/2016 | Kempe | A61N 1/36025 |

OTHER PUBLICATIONS

Segrace, R.A. et al. "Concurrent Cognitive Control Training Augments the Antidepressant Efficacy of TDCS: A Pilot Study." Brain Stimulation 7.2 (2014): 325-31. Web.*

Castano-Candamil, Ssebastian et al. "Solving the EEG Inverse Problem Based on Space-Time-Frequency Structured Sparsity Constraints." Neuroimage 118 (2015) 598-612. Web.*

Marshall, L. "Transcranial Direct Current Stimulation during Sleep Improves Declarative Memory." Journal of Neuroscience 24.44 (2004): 9985-992. Web.*

Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.*

Sahlem, Gregory L., et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.*

Barham, Michael P., Peter G. Enticott, Russell Conduit, and Jarrad A.g. Lum. "Transcranial Electrical Stimulation during Sleep Enhances Declarative (but Not Procedural) Memory Consolidation: Evidence from a Meta-analysis." Neuroscience & Biobehavioral Reviews 63 (2016): 65-77. Web.*

Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.*

Westerberg, Carmen E., Susan M. Florczak, Sandra Weintraub, M.-Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.*

McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.

Marshall L., Helgadóttir H, Mölle M, Born J. Boosting slow oscillations during sleep potentiates memory. Nature. 2006;444: pp. 610-613.

Javadi AH, Walsh V. Transcranial direct current stimulation (tDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science. 2007;315: pp. 1426-1429.

Rudoy JD, Voss, JL, Westerberg CE, Paller KA. Strengthening Individual Memories by Reactivating Them During Sleep. Science. 2009;326: p. 1079.

Bendor D, Wilson MA. Biasing the content of hippocampal replay during sleep. Nat. Neurosci. 2012;15: pp. 1439-1444.

Abeyratne UR, Swamkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007, 318 (5853): pp. 1147-1150.

The SenseWear armband as a Sleep Detection Device [Internet]. [cited Nov. 23, 2014]. pp. 1-9. Available from: http://www.bodymedia.com/Professionals/Whitepapers/The-SenseWear-armband-as-a-Sleep-Detection-Device?whence=.

Ruffini et al., Optimization of multifocal transcranial current stimulation for weighted cortical pattern targeting from realistic modeling of electric fields, Neuroimage, 89:216-25, 2014.

Rissman and Wagner, "Distributed Representations in Memory: Insights from Functional Brain Imaging," Annual Rev Psychol, 63: 101-128, 2012.

Rolls, "The Mechanisms for Pattern Completion and Pattern Separation in the Hippocampus," Frontiers in Systems Neuroscience, 7: 74, 2013.

McHugh et al, "Dentate Gyrus NMDA Receptors Mediate Rapid Pattern Separation in the Hippocampal Network," Science, 317(5834): 94-99, 2007.

Grech, R., Cassar, T., Muscat, J., Camilleri, K.P., Fabri, S.G., Zervakis, M., Xanthopoulos, P., Sakkalis, V. and Vanrumste, B., 2008. Review on solving the inverse problem in EEG source analysis. Journal of neuroengineering and rehabilitation, 5(1), pp. 1-33.

Tucker DM. Spatial sampling of head electrical fields: the geodesic sensor net. Electroencephalogr. Clin. Neurophysiol, 87: pp. 154-163, 1993.

Michel C., Murray MM. Towards the utilization of EEG as a brain imaging tool, NeuroImage 61 (2012), pp. 371-385.

Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.

Dmochowski JP, Datta A, Bikson M, Su Y, Parra LC. Optimized multi-electrode stimulation increases focality and intensity at target. J. Neural Eng., 8:046011, 2011, pp. 1-16.

Jones DK and Leemans A, "Diffusion Tensor Imaging", Methods in Molecular Biology 711: pp. 127-144, 2011.

Ramírez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.

Michael Schirner, et al., "An automated pipeline for constructing personalized virtual brains from multimodal neuroimaging data," NeuroImage, vol. 117, Aug. 15, 2015, pp. 343-357.

Nader K, Schafe GE, Le Doux JE. Fear memories require protein synthesis in the amygdala for reconsolidation after retrieval. Nature. 2000; 406: pp. 722-726.

Dudai Y. The neurobiology of consolidations, or, how stable is the engram? Annu. Rev. Psychol. 2004; 55: pp. 51-86.

Squire LR, Alvarez P. Retrograde amnesia and memory consolidation: a neurobiological perspective. Curr. Opin. Neurobiol. 1995; 5: pp. 169-177.

Foa EB. Social anxiety disorder treatments: psychosocial therapies. J. Clin. Psychiatry. 2006; 67 Suppl 12: pp. 27-30.

Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.

Bustos SG, Maldonado H, Molina VA. Midazolam disrupts fear memory reconsolidation. Neuroscience. 2006; 139: pp. 831-842.

Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.

(56) References Cited

OTHER PUBLICATIONS

Soterix Medical Website. High Definition-transcranial Direct Current Stimulation (HD-tDCS) [Internet]. Available from: http://soterixmedical.com/hd-tdcs, downloaded Aug. 8, 2016, pp. 1-13.
Chan JCK, LaPaglia JA. Impairing existing declarative memory in humans by disrupting reconsolidation. Proc. Natl. Acad. Sci. 2013;110: pp. 9309-9313.
Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.
Euston DR, Gruber AJ, McNaughton BL. The role of medial prefrontal cortex in memory and decision making. Neuron. 2012; 76: pp. 1057-1070.
Ji D, Wilson MA. Coordinated memory replay in the visual cortex and hippocampus during sleep. Nat. Neurosci. 2007; 10: pp. 100-107.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.
Dmochowski JP, Datta A, Bikson M, Su Y, Parra LC. Optimized multi-electrode stimulation increases focality and intensity at target. J. Neural Eng. 2011; 8:pp. 046011-1-046011-16.
Edmund Rolls, "The mechanisms for pattern completion and pattern separation in the hippocampus," Front Syst Neurosci. Oct. 2013; vol. 7: Article 74, pp. 1-21.
Thomas J. McHugh, et al., "Dentate Gyrus NMDA Receptors Mediate Rapid Pattern Separation in the Hippocampal Network," Science, vol. 317, (Jul. 2007); pp. 94-99.
Jesse Rissman, et al., "Distributed representations in memory: Insights from functional brain imaging," Annu Rev Psychol. 2012 ; 63: pp. 101-128.
Giulio Ruffinia, et al., "Optimization of multifocal transcranial current stimulation for weighted cortical pattern targeting from realistic modeling of electric fields," Neuroimage. Apr. 1, 2014; 89: pp. 216-225.
Office Action 1 for U.S. Appl. No. 15/072,353, dated Oct. 19, 2016.
Tremblay, Sara, et al., "The uncertain outcome of prefrontal TDCS," Brain Stimulation 7.6 (2014): pp. 773-783. Web.
Segrave, R.A., et al., "concurrent cognitive control training augments the anidepressant efficacy of TDCS: A pilot study," Brain Stimulation 7.2 (2014): pp. 325-331. Web.
Castano-Candamil, Sebastian, et al., "Solving the EEG inverse problem based on space-time-frequency structured sparsity constraints," Neuroimage 118 (2015), pp. 598-612. Web.
Response to Office Action 1 for U.S. Appl. No. 15/072,353, dated Feb. 17, 2017.
Office Action 2 for U.S. Appl. No. 15/072,353, dated Apr. 24, 2017.
Krause, M. R., Zanos, T. P., Csorba, B. A., Pilly, P. K., Choe, J., Phillips, M. E., Datta, A., and Pack, C. C. (2017). Transcranial direct current stimulation facilitates associative learning and alters functional connectivity in the primate brain. Current Biology, 27(3), pp. 3086-3096.

* cited by examiner

METHOD TO ENHANCE SPECIFIC MEMORIES WITH TCS DURING SLOW-WAVE SLEEP

CROSS-REFERENCE TO RELATED APPLICATIONS

This is a Non-Provisional Application of U.S. Provisional Patent Application No. 62/210,907, filed in the United States on Aug. 27, 2015, entitled, "Method to Enhance Specific Memories with tCS During Slow-Wave Sleep," the entirety of which is incorporated herein by reference.

This is also a Non-Provisional Application of U.S. Provisional Patent Application No. 62/210,890, filed in the United States on Aug. 27, 2015, entitled, "Transcranial Intervention to Weaken Traumatic Memories," the entirety of which is incorporated herein by reference.

This is ALSO a Non-Provisional Application of U.S. Provisional Application No. 62/247,435, filed in the United States on Oct. 28, 2015, entitled, "Mapping Transcranial Signals to Transcranial Stimulation Required to Reproduce a Brain State," the entirety of which is incorporated herein by reference.

BACKGROUND OF INVENTION

(1) Field of Invention

The present invention relates to a system for reactivating a sensed brain activation pattern and, more particularly, to a system for reactivating a sensed brain activation pattern by learning a mapping between the sensed brain activation pattern and an applied stimulation.

(2) Description of Related Art

Memories acquired during the day are encoded into the hippocampus ("one-shot learning") and consolidated at night during slow-wave sleep (SWS). During SWS, random synchronized cortical inputs to the hippocampus cue a recall, and train the slow-learning, long-term storage in cortex. Consolidation to long-term memory can take from weeks to as long as a year.

Learning new things quickly always takes effort. If the new things are fun or there is emotional involvement, neurotransmitters (e.g., dopamine) are naturally released to make it seem effortless to store a memory of an event (see the List of Incorporated Literature References, Literature Reference No. 1). However, this facilitatory neuromodulation is not guaranteed for every experience that must be critically remembered. Prior art has attempted non-specific memory enhancement with weak current stimulation, guided by a coarse understanding of the underlying neural processes to just the prefrontal cortex (PFC) (see Literature Reference Nos. 2 and 3).

The prior art for enhancing specific memories in healthy humans by manipulating the memory consolidation process is to present particular external cues during sleep (see Literature References No. 4 and 5). For example, the researchers of Literature Reference No. 4 achieved approximately 13% improvement in the memory retention of locations of 15 visual objects on a two-dimensional grid after 8 hours of sleep when subjects were exposed, during slow-wave sleep (SWS), to the odor (e.g., smell of a rose) that was present in the background during learning.

Similarly, the researchers of Literature Reference No. 5 demonstrated approximately 17% improvement in the memory retention of locations of 25 objects using 25 different sound cues (e.g., meow for cat, whistle for kettle). A 3.5 min sequence of the 25 sound cues was played during SWS. Note that in these studies the manipulator cues became part of the declarative memories that were being enhanced, thereby corrupting them in a way. Using neural ensemble recordings in the rat hippocampus, Literature Reference No. 6 described that the representation of a background cue or a memory component during SWS (that does not disrupt the sleep) can preferentially increase the incidence of reactivations, or replays, corresponding to the memory of interest to selectively enhance its consolidation. The method arising from the study of Literature Reference No. 6, which employs a task-related cue to bias the consolidation process, works for only those associations that comprise at least one auditory or olfactory attribute.

Thus, a continuing need exists for a system that will enhance the proportion of SWS during non-REM sleep to ensure a sufficiently high number of consolidation cycles to strengthen the memory without the need for association with a task-irrelevant auditory or olfactory cues.

SUMMARY OF THE INVENTION

The present invention relates to a system for reactivating a sensed brain activation pattern and, more particularly, to a system for reactivating a sensed brain activation pattern by learning a mapping between the sensed brain activation pattern and an applied stimulation. The system comprises one or more processors and a memory having instructions such that when the instructions are executed, the one or more processors perform multiple operations. The system detects, via at least one sensor, brain activity of a user as the user learns a new episode pattern or recalls an episode pattern. The episode pattern is temporally compressed, resulting in a temporally compressed episode pattern. Then, a specific sleep stage in the user is detected. Upon detection of the specific sleep stage, the system automatically recreates the temporally compressed episode pattern by applying neural stimulation to the user to ensure the consolidation of the episode pattern in the user.

In another aspect, a set of neural signals related to the episode pattern are recreated in a subconscious form that is temporally compressed to match a cortical replay speed during slow-wave sleep.

In another aspect, if needed, the system apples transcranial alternating current stimulation (tACS) to the prefrontal cortex of the user during non-rapid eye movement (REM) sleep for enhancing and prolonging slow-wave sleep.

In another aspect, a mapping is created to generate current brain activity in three-dimensional voxels.

In another aspect, the system detects a non-REM sleep stage in the user, and determines whether the user is in a slow-wave sleep stage. If the user is not in a slow-wave sleep stage, slow-wave sleep is automatically induced using transcranial alternating current stimulation (tACS). A difference between current brain activity of the user, as measured by at least one sensor, and the temporally compressed episode pattern is computed. A required neural stimulation to force specific memory replay is then computed based on the difference between the current brain state of the user and the temporally compressed episode pattern. The required neural stimulation is applied to the user.

In another aspect, the neural stimulation comprises low levels of spatiotemporally patterned high definition transcranial current stimulation (HD-tCS).

In another aspect, the neurostimulation is applied using a transcranial stimulation cap.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
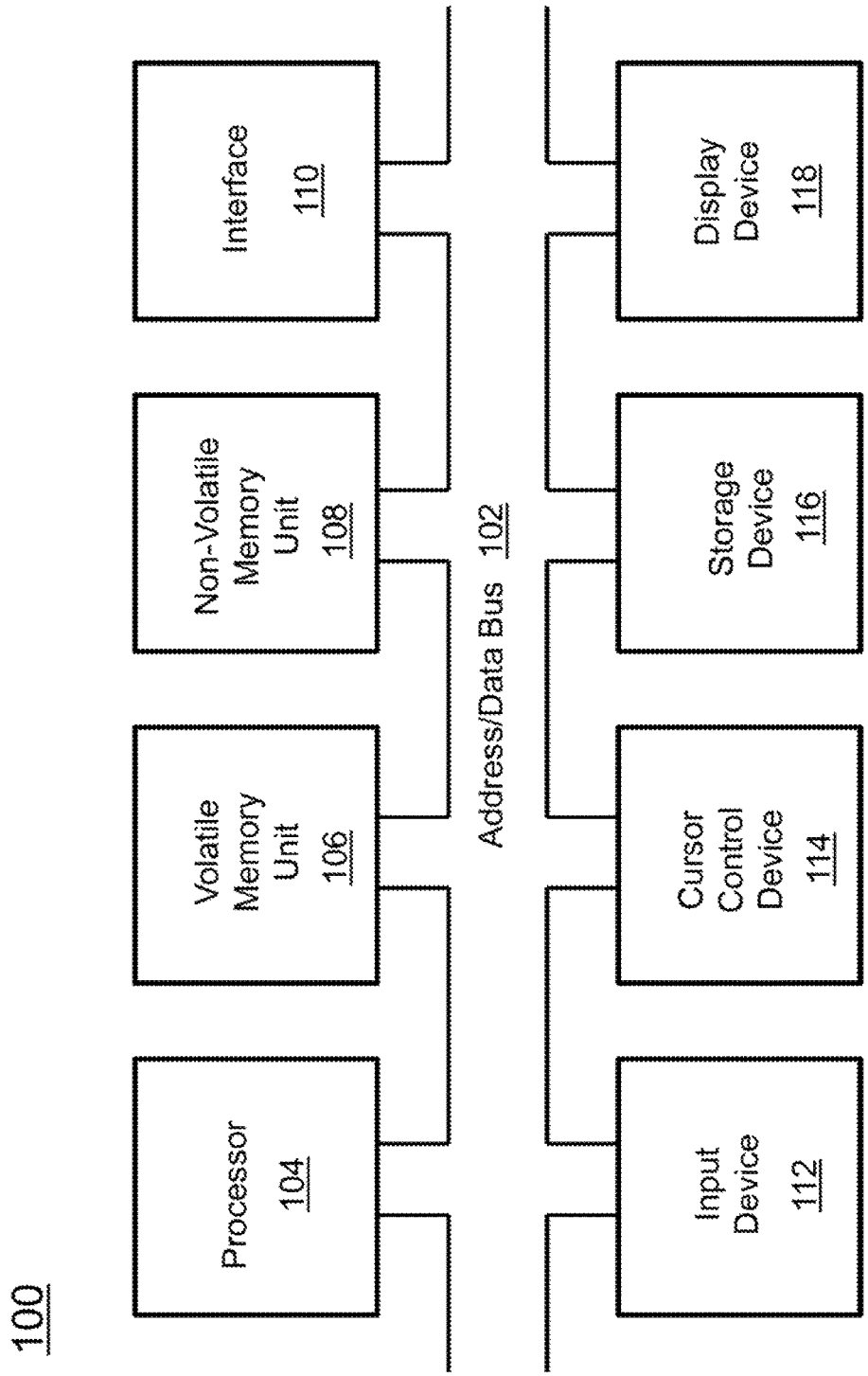
FIG. 1 is a block diagram depicting the components of a system for reactivating a sensed brain activation pattern according to various embodiments of the present disclosure.

The present invention relates to a system for reactivating a sensed brain activation pattern and, more particularly, to a system for reactivating a sensed brain activation pattern by learning a mapping between the sensed brain activation pattern and an applied stimulation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

Before describing the invention in detail, first a list of cited literature references used in the description is provided. Next, a description of various principal aspects of the present invention is provided. Finally, specific details of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully included herein. The references are cited in the application by referring to the corresponding literature reference number, as follows:

1. McNamara C G, Tejero-Cantero A, Trouche S, Campo-Urriza N, Dupret D. Dopaminergic neurons promote hippocampal reactivation and spatial memory persistence. Nat Neurosci. 2014; 17:1658-60.
2. Marshall L, Helgadóttir H, Mölle M, Born J. Boosting slow oscillations during sleep potentiates memory. Nature. 2006; 444:610-3.
3. Javadi A H, Walsh V. Transcranial direct current stimulation (tDCS) of the left dorsolateral prefrontal cortex modulates declarative memory. Brain Stimulat. 2012; 5:231-41.
4. Rasch B, Büchel C, Gais S, Born J. Odor cues during slow-wave sleep prompt declarative memory consolidation. Science. 2007; 315:1426-9.
5. Rudoy J D, Voss J L, Westerberg C E, Paller K A. Strengthening Individual Memories by Reactivating Them During Sleep. Science. 2009; 326:1079-1079.
6. Bendor D, Wilson M A. Biasing the content of hippocampal replay during sleep. Nat Neurosci. 2012; 15:1439-44.
7. Euston D R, Gruber A J, McNaughton B L. The role of medial prefrontal cortex in memory and decision making. Neuron. 2012; 76:1057-70.
8. Ji D, Wilson M A. Coordinated memory replay in the visual cortex and hippocampus during sleep. Nat. Neurosci. 2007; 10:100-7.
9. Abeyratne U R, Swarnkar V, Rathnayake S I, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007; 2007:709-12.

10. Salmi T, Brander P E. Computer assisted detection of REM and non-REM sleep for analysis of nocturnal hypoxaemia in patients with ventilatory impairment. Int. J. Clin. Monit. Comput. 1994; 11:63-70.
11. Sunseri et al. The SenseWear™ armband as a Sleep Detection Device. BodyMedia, Inc. 2014.
12. Euston et al. Fast-Forward Playback of Recent Memory Sequences in Prefrontal Cortex During Sleep. Science. November 2007; 318 (5853): 1147-1150.
13. Dmochowski J P, Datta A, Bikson M, Su Y, Parra L C. Optimized multi-electrode stimulation increases focality and intensity at target. J. Neural Eng. 2011; 8:046011.
14. Ramirez R, Makeig S. Neuromagnetic source imaging of spatiotemporal brain dynamical patterns using frequency domain independent vector analysis (IVA) and geodesic sparse Bayesian learning (gSBL). Chicago, Ill.: Organization for Human Brain Mapping, 2007.
15. Wong P. Introduction to Brain Topography. New York, N.Y., USA: Plenum Press, 1991.
16. Jones D K and Leemans A, "Diffusion Tensor Imaging", Methods in Molecular Biology 711:127-144, 2011.
17. Wolters C H, Anwander A, Tricoche X, Weinstein D, Koch M A, MacLeod R S. Influence of tissue conductivity anisotropy on EEG/MEG field and return current computation in a realistic head model: a simulation and visualization study using high-resolution finite element modeling. NeuroImage. 2006; 30:813-26.

(2) Principal Aspects

The present invention has three "principal" aspects. The first is a system for reactivating a sensed brain activation pattern. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. For example, the input device 112 may include one or more sensors, such as a camera for video or still images, a microphone, or a neural sensor. Other example input devices 112 may include an accelerometer, a GPS sensor, or a gyroscope.

In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
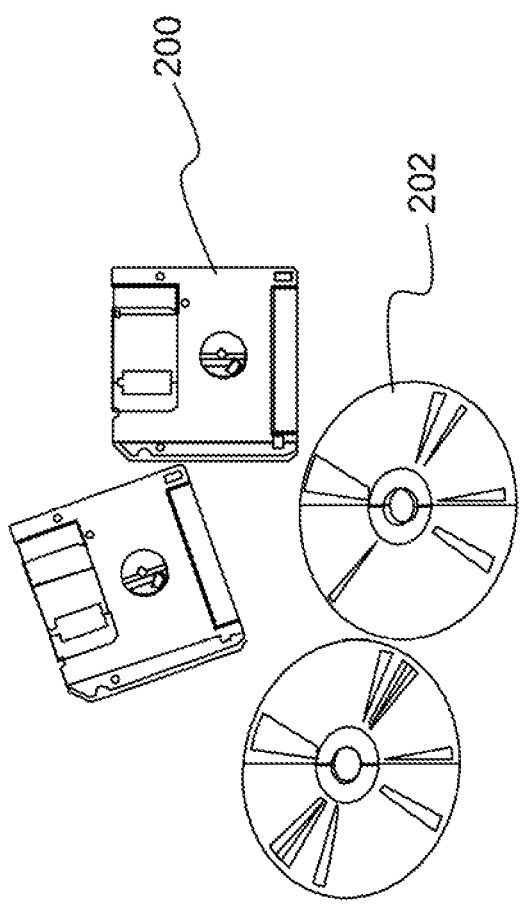
FIG. 2 is an illustration of a computer program product according to various embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Specific Details of the Invention

Memories acquired during the day are encoded into the hippocampus ("one-shot learning") and consolidated at night during slow-wave sleep (SWS). During SWS, random synchronized cortical inputs to the hippocampus cue a recall and train the slow-learning, long-term storage in the cortex. Consolidation to long-term memory can take from weeks to as long as a year. Described herein is a system to externally stimulate and control this consolidation process at just the right stage of sleep. It will use targeted transcranially-applied electrical stimulation, called high-definition transcranial current stimulation (HD-tCS), to affect memory-specific cortical replays periodically during non-REM (rapid eye movement) sleep, at a much higher rate than random.

Figure 3:
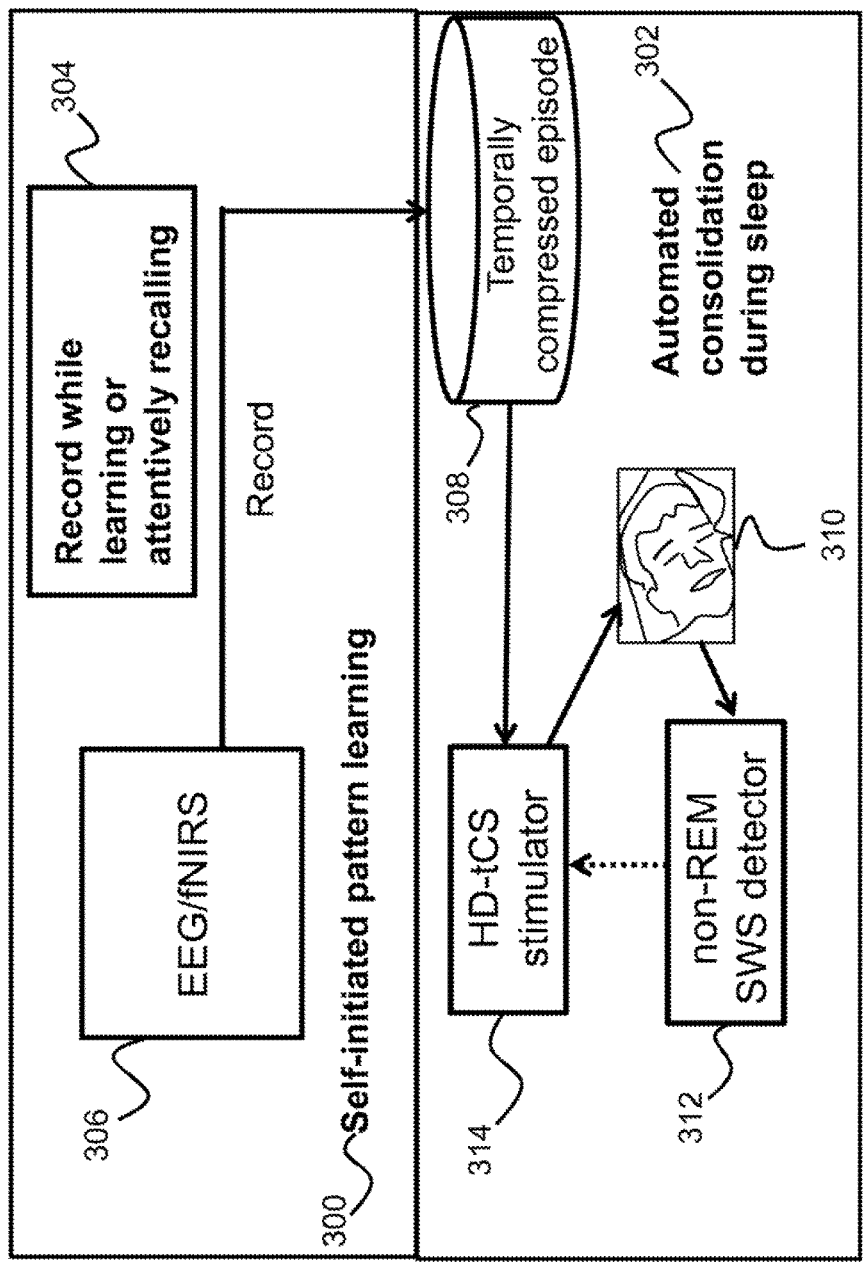
FIG. 3 is a flow diagram illustrating an overview of a system for reactivating a sensed brain activation pattern according to various embodiments of the present disclosure.

The system according to various embodiments of the present disclosure is illustrated in FIG. 3, which depicts stages of self-initiated pattern learning 300 and automated consolidation during sleep 302. As a human subject learns/encodes a specific memory (i.e., experiences a particular episode) or attentively recalls it, he initiates a recording of spatiotemporally distributed brain activity (i.e., record while learning or attentively recalling 304) using sensors, such as high-resolution EEG (electroencephalogram) and fNIRS (functional near-infrared spectroscopy) sensors 306. This is called the "episode pattern". The episode pattern is then temporally compressed (i.e., temporally compressed episode 308) to the speed of cortical replays during SWS. At night, the subject 310 wears a transcranial stimulation cap fitted with transcranial EEG/fNIRS sensors 306 and HD-tCS electrodes. When non-REM slow-wave sleep is detected via a non-REM SWS detector 312, the system recreates the temporally compressed episode 304 pattern across the cortical areas in the brain by applying low levels of spatiotemporally patterned HD-tCS via a HD-tCS stimulator 314 to the subject 310.

The subject 310 can employ the system according to various embodiments of the present invention at home during waking and sleep. tCS is safe (e.g., electrode current intensity to area ratio of about 0.3-5 A/m2 (amperes per square meter)) and applied at lower frequencies (typically <1 kilohertz (kHz)), resulting in weak electric fields in the brain (with amplitudes of about 0.2-2 V/m (volts per meter). This procedure, using transcranial electrical stimulation to enhance specific memories, is a unique aspect of this disclosure. The present invention employs a unique procedure for learning a mapping between a transcranially sensed brain activation pattern and the required transcranially applied stimulation to reactivate that pattern in the brain.

The approach described herein is to record spatiotemporally distributed brain activity (i.e., record while learning or attentively recalling 304) while the subject 310 learns some new specific information, or recalls a just-learned episode in his mind. Then, when the subject is in non-REM slow-wave sleep, a temporally compressed version of this pattern (i.e., temporally compressed episode 308) can be activated by using safe, low levels of high-definition transcranial current stimulation (HD-tCS) via the HD-tCS stimulator 314, thereby triggering and ensuring the consolidation of the particular episode under consideration to strengthen the corresponding memory.

Described below are the procedures and apparatus for recording an episode pattern and for sleep therapy according to various embodiments of the present invention. Also described is how the stimulation parameters required to recreate the episode pattern are found. In addition, a method to use a sleep detector to recognize non-REM sleep and automatically invoke the application of the episode pattern is described. Neural signals related to the episode are recreated in a subconscious form that is temporally compressed to match cortical replay speeds during slow-wave sleep. In subjects whose sleep structure has an impoverished duration of slow-wave sleep (SWS), the method according to embodiments of the present invention has the facility to apply transcranial alternating current stimulation (tACS) at ~1 Hertz (Hz) to the prefrontal cortex (PFC) during non-REM sleep for inducing SWS.

Figure 4:
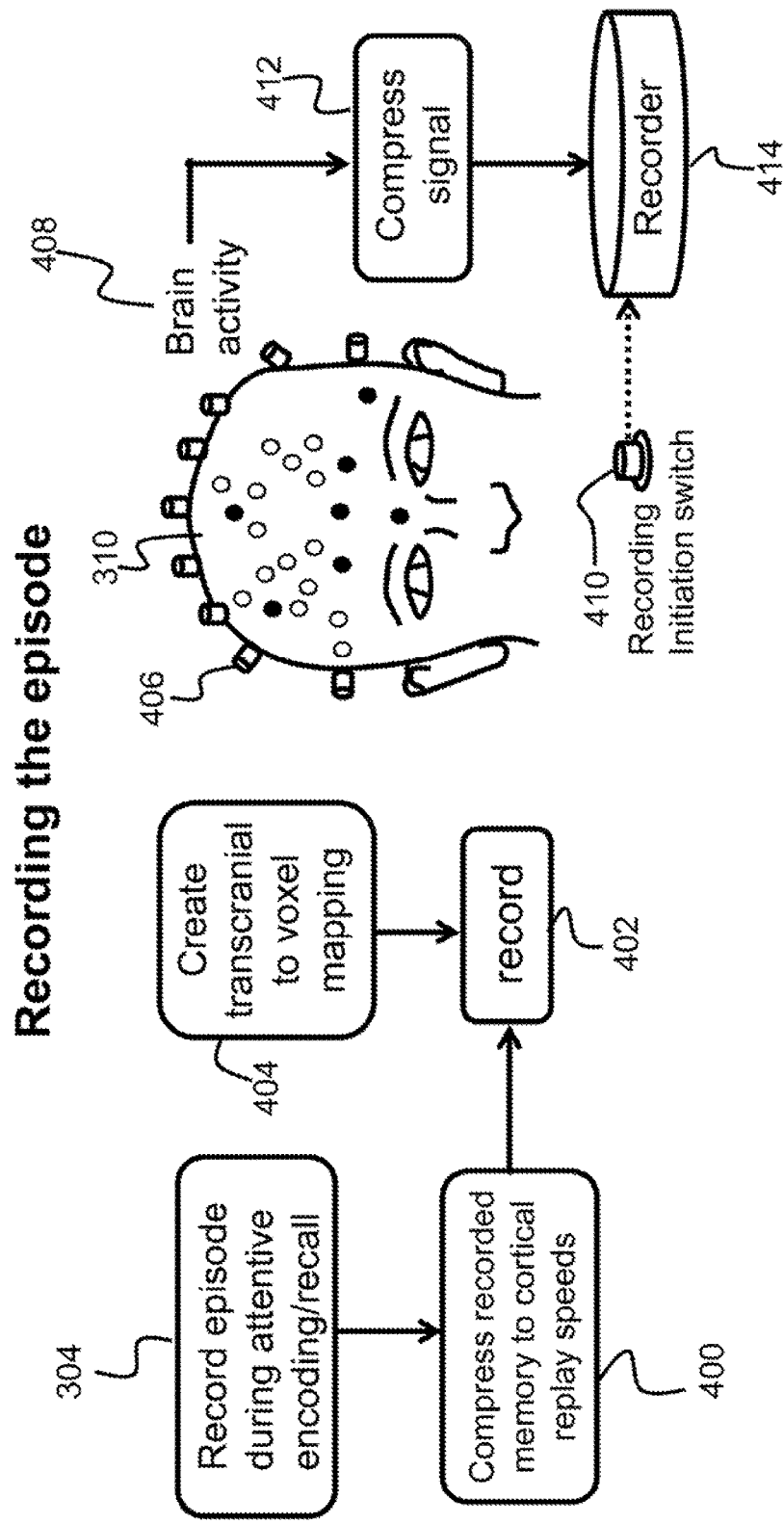
FIG. 4 illustrates the procedure and setup for recording an episode according to various embodiments of the present disclosure.

FIG. 4 illustrates the setup for subject-initiated recording of the specific memory ("episode") to enhance its consolidation during subsequent sleep. A system flow diagram on the left illustrates the procedure, and the setup for recording the episode is shown on the right. As depicted on the left of FIG. 4, the system records an episode during attentive encoding (learning) or recall 304. The recorded memory is compressed to cortical replay speeds 400. The recorded memory needs to be compressed by a factor of 6 to 7 to achieve cortical replay speeds during sleep. The range of compression factors is known to those skilled in the art. Cortical replay speeds were identified in rat studies, where rats traversed certain routes, causing certain neurons, called "place cells", to fire in sequence, representing the sequence of locations they moved in. During subsequent sleep, it was observed that those neurons fired, in the same sequence, at a much higher rate of speed (see Literature Reference No. 12). During recording 402 of the compressed episode pattern (or memory), a transcranial to voxel mapping is created 404, as will be described in further detail below.

As shown on the right side of FIG. 4, the subject 310 wears a high-density array of sensors 406 and stimulators on the head, containing sensors such as EEG (electroencephalogram) and fNIRS (functional near-infrared spectroscopy), and electrical stimulators, such as HD-tCS. The recording of the brain activity 408, sensed via the sensors 406, is initiated via, for instance, a recording initiation switch 410. The array of sensors 406 can be a high-resolution sensor array distributed over the head of the subject 310. The brain activity 408 signals are compressed 412 and stored in a recorder 414.

Figure 5:
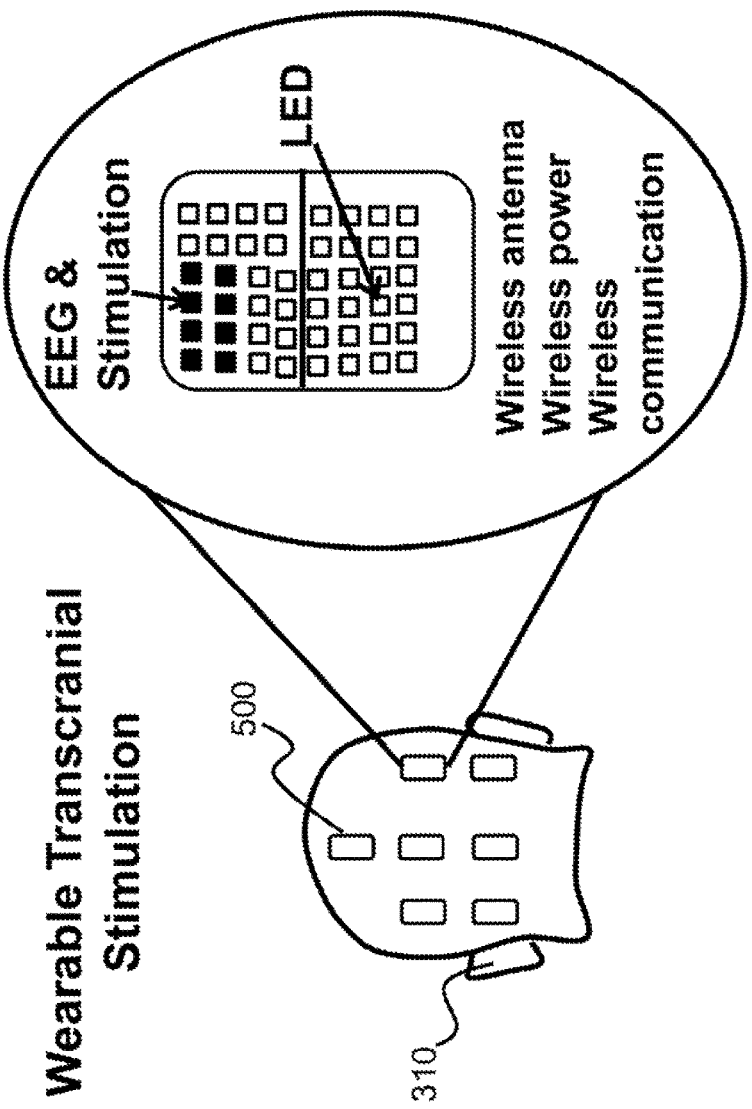
FIG. 5 illustrates an example of wearable transcranial stimulation according to various embodiments of the present disclosure.

The sensor/stimulator array 500 comprising a plurality of sensors can be engineered in an ergonomic design such as the one shown in FIG. 5. For example, MC-10, Inc. makes conformal, nearly invisible, stretchy electronics that could be used in the present invention. MC-10, Inc. is located at 10 Maguire Road Building 3, 1st Floor, Lexington, Mass. 02421. Each array 500 can comprise any of the following: light emitting diode (LED), EEG sensors, and electrical stimulators. Further, the array 500 can include a wireless antenna, wireless power, and wireless communication.

Figure 6:
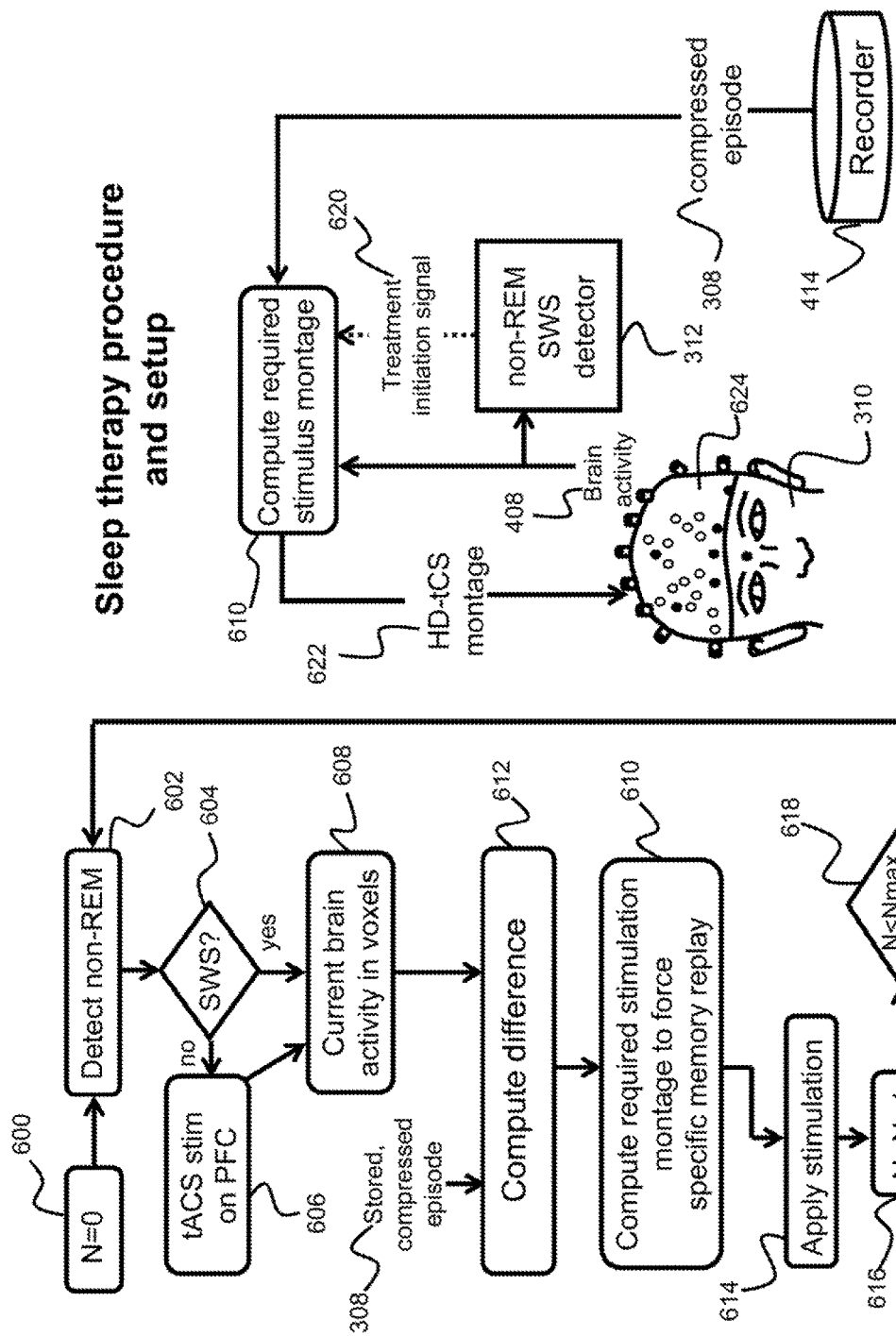
FIG. 6 illustrates the procedure and setup for sleep therapy according to various embodiments of the present disclosure.

In the flow diagram of FIG. 6, a mapping from brain signals sensed transcranially (by sensors like EEG and fNIRS) to the most likely causal brain activity in three-dimensional (3D) voxels of the brain volume is created. This is a problem known in the art as blind source separation, which discovers the most likely distributed sources of the activity within the head from the recordings at the scalp electrodes. Then, the transcranial stimulation montage required to reproduce this brain activity pattern across the neocortex must be computed.

External brain sensors, such as electroencephalogram (EEG), receive signals from the scalp that indicate activity on the surface of the brain. It has long been recognized that the EEG can be analyzed to infer the activity in the three-dimensional (3D) volume of the brain that could have caused the particular surface signals sensed by EEG, using topographic maps and spatial pattern analysis methods as well as source localization techniques (see Literature Reference No. 15). Non-invasive (transcranially applied) electrical stimulation of the brain has been shown in prior art to modulate neuronal activity and synchrony across multiple brain areas and, thereby, to enhance various behaviors.

Described herein is a technique to compute a stimulation montage that can be applied by transcranial stimulation electrodes to reproduce a brain state that was previously sensed by EEG and/or functional near infrared sensing (fNIRS). This requires mapping the externally sensed signals to the most likely set of 3D sources of activity in the brain and then computing an electrical stimulation montage required to transform the current brain state into the desired brain state. The system according to embodiments of the present disclosure uses diffusion tensor imaging (DTI) data to link EEG sources with stimulation-induced current flows in the brain volume, which are different modalities. DTI provides average orientation and density of white matter tracts in each voxel, which are used to convert induced electric fields into neural activity changes.

Based on T1- and T2-weighted magnetic resonance images (MRIs) of a human subject, finite element modeling is used to build a personalized forward model of voltage fluctuations recorded at the EEG/fNIRS electrodes on the scalp (as described in Literature Reference No. 17), as well as a personalized forward model of transcranial stimulation (tCS)-induced current density distributions in the brain volume (see Literature Reference No. 13 for a description of tCS-induced current density distributions). Multi-scale geodesic Sparse Bayesian Learning is used with a Laplacian prior for subject-specific inverse modeling to localize the distributed sources for the transcranially recorded EEG/fNIRS signals (see Literature Reference No. 14).

To determine the stimulation required to reproduce a particular activity pattern across the neocortex, the difference in activity for each voxel of the brain between the desired activity pattern and the current pattern was first computed. Based on diffusion tensor imaging (DTI) data of the subject, which provides fine-grained information on the white matter fiber orientation and density, one can compute the necessary electric field to achieve the desired activity change in each voxel. With the volumetric distribution of desired electric fields within the brain and the material properties of the scalp electrodes, as well as various tissue category masks in the brain volume, any of several types of optimization techniques can be employed to solve for the stimulation montage (such as the technique described in Literature Reference No. 13).

A point neuron activation function models the electrophysiological properties of real neurons, while simplifying their geometry to a single point. The neural activity S tends to increase linearly as a function of applied negative current I (i.e., the current out of a neuron, which moves negative charges away and increases positive potential). If one assumes the gain factor G stays constant during application of the stimulation, and the activity change desired in a particular voxel is $\Delta S$, then the amount of current that needs to be applied along the axis of the neurons in the voxel is $I=\Delta S/G$. To determine the gain factors of various voxels for a given subject, one embodiment of the present disclosure is to arrive at them by applying various stimulation montages and measuring the corresponding affected activity changes across the brain volume. The gain factors in each voxel need to be scaled by the cosine of the angle between the dominant white matter tract orientation and the induced electric field. One skilled in the art can perform this procedure in a straightforward manner.

The procedure is summarized below. Steps 1-4 below create a model of desirable brain activity in the relevant voxels of the brain. This is a prerequisite to using the model to compute required brain stimulations to recreate a desired brain state. One example of a desired brain state is a state in which the subject's behavioral response to a certain experience is either enhanced or reduced. For instance, it could be beneficial to become more sensitive to threats of certain types. In the case of post-traumatic stress disorder, it is desirable to reduce anxiety triggered by certain benign events. Another non-limiting example is to enhance memory function in a person whose brain is improperly storing and recalling memories. In particular, step 2 must be done when the subject is in a desired brain state. For instance, in the case of post-traumatic stress disorder (PTSD), it is desirable to reduce anxiety triggered by certain benign events. Therefore, the desired brain state for a PTSD patient is one in which the subject is calm with low anxiety. Such a brain state can be achieved when the patient is in a quiet, safe place. Breathing exercises together with yoga or meditation are known to lower stress and may be used. Alternatively, calming videos such as the ones used by some airlines to settle passengers down before a long trip (e.g., wildlife scenes accompanied by relaxing music) may also be used.

1. Take T1- and T2-weighted MRIs and a DTI of the subject (as described in detail in Literature Reference No. 16).
2. During a desired brain state, record brain activity using EEG/fNIRS electrodes on the scalp.
3. Use finite element modeling based on the MRIs of step 1 to build a personalized forward model that describes how, for this subject, neural activity in the voxels of the brain create electrical signals that can be sensed on the surface of his skull, as described in Literature Reference No. 17.
4. Use multi-scale geodesic Sparse Bayesian Learning with a Laplacian prior for subject-specific inverse modeling to localize the distributed sources for the transcranially recorded (in step 2) EEG/fNIRS signals of the desired brain state, as described in Literature Reference No. 14. This provides desired activities in each voxel of the brain volume. In many cases, only a few brain regions are relevant for a particular use, the voxels can now be limited to a "relevant set".
5. Subsequently, once steps 1-4 are completed, and when the subject is in an undesirable brain state, record brain activity as in step 2.
6. Repeat step 4 for the undesired brain state.
7. Compute the difference in activity for each relevant voxel of the brain between the desired activity pattern and the current pattern.
8. Translate the desired activity change in each voxel into the necessary electric field, properly aligned to the orientation of the nerve fibers based on DTI data, to achieve the desired activity pattern.
9. With the volumetric distribution of desired electric fields within the brain, and the material properties of the scalp electrodes as well as various tissue category masks in the brain volume having been characterized, an optimization technique is employed to solve for the stimulation montage to create the desired activity change of step 8, analogous to beam-forming but imposing additional limits on the maximum injected current due to safety. In one embodiment, the optimization technique described in Literature Reference No. 13 is implemented. However, as can be appreciated by one skilled in the art, additional suitable methods exist that could be used to solve for the stimulation montage.
10. With the volumetric distribution of desired electric fields within the brain, and the material properties of the scalp electrodes as well as various tissue category masks in the brain volume having been characterized, any of several types of optimization techniques are employed to solve for the stimulation montage to create the desired activity change of step 8 (e.g., Literature Reference No. 13).
11. Apply the stimulation montage and repeat steps 5-9 as needed.

The subject 310 initiates a recording of brain activity 408 (e.g., by pushing a recording initiation switch 410 as illustrated in FIG. 4) either while learning a new episode, or while recalling an episode attentively. Brain activity 408 from the transcranial sensors 406 is temporally compressed (compress signal 412) to cortical replay speeds using a generic compression factor of six to seven (see Literature Reference No. 7 for a description of compression factors). Cortical replay occurs at a faster rate than the waking experience; individual subjects may have different cortical replay rates (see Literature Reference Nos. 7 and 8 for a description of cortical replay rates), so replay rates will be adjusted up and down to find the best match.

FIG. 6 illustrates the flow chart and the setup for automated operation during sleep. As shown on the left, the process starts at N=0 (element 600), where N represents an episode pattern replay. A classifier detects a non-REM sleep stage 602 and determines whether the subject is in a SWS sleep stage 604. If not, the system automatically initiates therapy by computing and applying the stimulus required to reproduce the specific memory by changing the current brain activity (i.e., tACS stimulation on the prefrontal cortex (PFC) 606. The NREM (non-REM) sleep stage 602 detection is well studied, as described in Literature Reference Nos. 9 and 10, and simple devices for home use are proliferating on the market, such as SenseWear (see Literature Reference No. 11)). The subject must attain stage 4 of non-REM sleep, also known as slow-wave sleep (SWS) 604. Once non-REM sleep stage 602 is detected, it is possible to enhance/prolong SWS 604 using tACS of the PFC 606 at ~1 Hz. This can be used if the subject experiences short or infrequent periods of SWS 604. Alternatively, the system can just wait until the subject naturally enters a SWS 604 period. A mapping is created to generate current brain activity in voxels 608.

In either case, while the subject is in SWS 604 stage of non-REM sleep, the system will conduct the therapeutic regimen, using HD-tCS to impinge the stored, compressed episode 308 pattern in a distributed montage. The required stimulation montage to force specific memory replay 610 is computed based on the difference between the current brain state of the subject and the compressed episode pattern to be reactivated (i.e., compute difference 612), and the stimulation is applied (i.e., apply stimulation 614). The process then proceeds to another episode replay (i.e., N=N+1 (element 616)) as long as N<Nmax (element 618). Nmax is a parameter of the system representing the number of times the system should attempt to replay the episode during sleep.

The decision about how to set Nmax can be left to the user; if set too high, it may not leave time for other, unrelated memories to consolidate. If set too low, it will take a long time to consolidate the specific memory the user is trying to learn. Another issue is that stimulation (element 614) should occur during non-REM, slow-wave sleep during UP states. UP states can be clearly detected in the EEG signals. After stimulating in an UP state, the system should wait at least 1 UP state without stimulating to allow time for the just-induced memory traces to consolidate.

On the right of FIG. 6 is an illustration of the setup of sleep therapy according to various embodiments of the present invention. As described above, the compressed episode pattern (or compressed signal in FIG. 4) is stored in a recorder 414 element. A plurality of sensors positioned on the head of the user 310 senses brain activity 408. A non-REM SWS detector 312 is used to detect a non-REM SWS stage in the user 310. Upon a treatment initiation signal 620 (e.g., recording initiation switch 410 in FIG. 4), the required stimulus montage is computed (i.e., compute required stimulation montage 610) as described above. The stimulus is applied via a HD-tCS montage 622 to the user 310. In one embodiment, the user 310 wears a transcranial stimulation cap 624 fitted with transcranial EEG/fNIRS sensors and HD-tCS electrodes.

In a first stage of transition of the present invention to real-world use would be a clinical system, for lab use. During this period, stimulation montages would be worked out and perfected. This would essentially require an individualized mapping between sensed EEG/fNIRS signals of a certain spatiotemporally distributed brain state and the tCS stimulation required to reactivate that brain state. Then, the patient could take home a transcranial sensing and stimulation system that would detect NREM sleep and apply the stimulation to enhance the consolidation of a particular memory. At this stage, it may be that each specific memory would have to be recorded and mapped at the clinic. Another stage would be a personal therapy system that can be operated at home by a naïve user with minimal supervision. Yet another stage would be a portable system will all the sensing and stimulation components miniaturized.

The system described herein can augment the natural process of forming strong memories when needed, especially for dull or boring things (e.g., high school homework), or if there are many things to learn in a short period of time, or the subject matter is complex. The targeted transcranial neurostimulation system according to embodiments of the present disclosure will speed the acquisition of new episodic and semantic knowledge without physical risk to the patient.

Additionally, the present invention can help with certain types of brain disorders that affect the ability to encode new memories, such as Alzheimer's disease, senility, or physical trauma, such as a concussion or traumatic brain injury (TBI)). Often medication, such as Aricept, is prescribed to sufferers of dementia. However, since it is a drug, there are side effects (e.g., interactions with certain heart rhythm disorders, prostate problems, asthma, and epilepsy). In contrast, the present invention requires no such pharmacological intervention and is directly applied to the brain with no interactions with other body systems. The invention described herein is an automated system that primarily operates during sleep. There is no need to depend on pharmacological drugs. Other benefits of the system are that it can be trained on an event (e.g., new information, memory) that is identified by the human subject. Further, the system can be automatically applied at night and does not require supervision.

What is claimed is:

1. A system for enhancing memories during sleep, the system comprising:
one or more processors and a non-transitory memory having instructions encoded thereon such that when the instructions are executed, the one or more processors perform operations of:
recording, via at least one transcranial sensor, transcranial sensor electrical signals during learning or recall of a memory;
using magnetic resonance imaging (MRI) data, mapping the transcranial sensor electrical signals to voxels of brain volume;
translating the mapped transcranial sensor electrical signals into an electric field by using an optimization technique to solve for the electric field;
upon detection of non-rapid eye movement (NREM) slow-wave sleep, applying, via a set of electrodes, the electric field.

2. The system as set forth in claim 1, wherein the recording of the transcranial sensor electrical signals is compressed to match a cortical replay speed during NREM slow-wave sleep.

3. The system as set forth in claim 2, wherein, if needed, the one or more processors further perform an operation of causing application of transcranial alternating current stimulation (tACS) to a prefrontal cortex during NREM sleep for enhancing and prolonging slow-wave sleep.

4. The system as set forth in claim 1, wherein the one or more processors further perform operations of:
if the user is not in a slow-wave sleep stage, then automatically inducing slow-wave sleep using transcranial alternating current stimulation (tACS).

5. The system as set forth in claim 1, wherein the electric field comprises low levels of spatiotemporally patterned high definition transcranial current stimulation (HD-tCS).

6. The system as set forth in claim 1, wherein the electric field is applied using a transcranial stimulation cap.

7. A computer-implemented method for enhancing memories during sleep, comprising:
an act of causing one or more processors to execute instructions stored on a non-transitory memory such that upon execution, the one or more processors perform operations of:
recording, via at least one transcranial sensor, transcranial sensor electrical signals during learning or recall of a memory;
using magnetic resonance imaging (MRI) data, mapping the transcranial sensor electrical signals to voxels of brain volume;
translating the mapped transcranial sensor electrical signals into an electric field by using an optimization technique to solve for the electric field;
upon detection of non-rapid eye movement (NREM) slow-wave sleep, applying, via a set of electrodes, the electric field.

8. The method as set forth in claim 7, wherein the recording of the transcranial sensor electrical signals is compressed to match a cortical replay speed during NREM slow-wave sleep.

9. The method as set forth in claim 8, wherein, if needed, the one or more processors further perform an operation of causing application of transcranial alternating current stimulation (tACS) to a prefrontal cortex during NREM sleep for enhancing and prolonging slow-wave sleep.

10. The method as set forth in claim 7, wherein the one or more processors further perform operations of:
if the user is not in a slow-wave sleep stage, then automatically inducing slow-wave sleep using transcranial alternating current stimulation (tACS).

11. The method as set forth in claim 7, wherein the electric field comprises low levels of spatiotemporally patterned high definition transcranial current stimulation (HD-tCS).

12. The method as set forth in claim 7, wherein the electric field is applied using a transcranial stimulation cap.

13. A computer program product for enhancing memories during sleep, the computer program product comprising:
computer-readable instructions stored on a non-transitory computer-readable medium that are executable by a computer having one or more processors for causing the processor to perform operations of:
recording, via at least one transcranial sensor, transcranial sensor electrical signals during learning or recall of a memory;
using magnetic resonance imaging (MRI) data, mapping the transcranial sensor electrical signals to voxels of brain volume;
translating the mapped transcranial sensor electrical signals into an electric field by using an optimization technique to solve for the electric field;

upon detection of non-rapid eye movement (NREM) slow-wave sleep, applying, via a set of electrodes, the electric field.

14. The computer program product as set forth in claim 13, wherein the recording of the transcranial sensor electrical signals is compressed to match a cortical replay speed during NREM slow-wave sleep.

15. The computer program product as set forth in claim 14, wherein, if needed, the one or more processors further perform an operation of causing application of transcranial alternating current stimulation (tACS) to a prefrontal cortex during NREM sleep for enhancing and prolonging slow-wave sleep.

16. The computer program product as set forth in claim 13, further comprising instructions for causing the one or more processors to perform operations of:

if the user is not in a slow-wave sleep stage, then automatically inducing slow-wave sleep using transcranial alternating current stimulation (tACS).

17. The computer program product as set forth in claim 13, wherein the electric field comprises low levels of spatiotemporally patterned high definition transcranial current stimulation (HD-tCS).

\* \* \* \* \*